United States Patent
Scotto et al.

(10) Patent No.: US 9,770,699 B2
(45) Date of Patent: Sep. 26, 2017

(54) METHOD FOR REVAMPING A SELF-STRIPPING UREA PLANT

(71) Applicant: Casale SA, Lugano (CH)

(72) Inventors: Andrea Scotto, Breganzona (CH); Paolo Bertini, Lugano (CH); Serena Gabbiadini, Milan (IT)

(73) Assignee: Casale SA (CH)

( * ) Notice: Subject to any disclaimer, the term of this patent is extended or adjusted under 35 U.S.C. 154(b) by 0 days.

(21) Appl. No.: 14/778,460

(22) PCT Filed: Mar. 5, 2014

(86) PCT No.: PCT/EP2014/054230
§ 371 (c)(1),
(2) Date: Sep. 18, 2015

(87) PCT Pub. No.: WO2014/154454
PCT Pub. Date: Oct. 2, 2014

(65) Prior Publication Data
US 2016/0288077 A1    Oct. 6, 2016

(30) Foreign Application Priority Data

Mar. 27, 2013  (EP) .................................... 13161428

(51) Int. Cl.
*B01J 10/00*    (2006.01)
*C07C 273/04*    (2006.01)

(52) U.S. Cl.
CPC ............. *B01J 10/00* (2013.01); *C07C 273/04* (2013.01); *B01J 2219/00024* (2013.01)

(58) Field of Classification Search
CPC ............. B01J 10/00; B01J 2219/00024; C07C 273/04
USPC .......................................................... 564/72
See application file for complete search history.

(56) References Cited

U.S. PATENT DOCUMENTS 5,403,956 A * 4/1995 Pagani .................. C07C 273/04
564/66

FOREIGN PATENT DOCUMENTS

| EP | 0 598 250 A1 | 5/1994 |
| EP | 2 128 129 A1 | 12/2009 |
| EP | 2 397 463 A1 | 12/2011 |
| GB | 1 542 371 | 3/1979 |
| WO | 2006/061083 A1 | 6/2006 |

OTHER PUBLICATIONS

International Search Report issued in connection with PCT/EP2014/054230, dated May 23, 2014.

* cited by examiner

*Primary Examiner* — Jafar Parsa
*Assistant Examiner* — Amy C Bonaparte
(74) *Attorney, Agent, or Firm* — Akerman LLP

(57) ABSTRACT

A method for revamping a self-stripping urea plant comprising the installation of a new CO2-stripping synthesis section (6), wherein at least part of the aqueous urea solution (10) leaving said new section (6) is directed to the existing low pressure recovery section (4) of the self-stripping plant, by-passing the existing self-stripping high-pressure section (2) and medium pressure treatment section (3).

10 Claims, 2 Drawing Sheets

METHOD FOR REVAMPING A SELF-STRIPPING UREA PLANT

This application is a national phase of PCT/EP2014/054230, filed Mar. 5, 2014, and claims priority to EP 13161428.1, filed Mar. 27, 2013, the entire contents of both of which are hereby incorporated by reference.

FIELD OF THE INVENTION

The present invention refers to a method for revamping of a self-stripping urea plant.

PRIOR ART

A disclosure of the self-stripping or thermal-stripping process and related plant can be found in GB 1542371. The process is also termed Snamprogetti after the name of its developer.

A self-stripping urea plant comprises basically a high-pressure (HP) synthesis loop, a medium-pressure (MP) section and a low-pressure (LP) recovery section.

The HP loop typically comprises a synthesis reactor, a steam-heated stripper, and a horizontal kettle condenser which operate substantially at the same pressure, usually around 140 to 160 bar. Ammonia and $CO_2$ are reacted in the synthesis reactor obtaining a urea aqueous solution, comprising ammonia and unconverted ammonium carbamate; said solution is heated in the high-pressure stripper to decompose the carbamate and recover ammonia; a vapour phase containing ammonia and $CO_2$ produced in the stripper is condensed in the high-pressure condenser, and recycled to said reactor. The stripping process takes place with the help of heat furnished e.g. by hot steam (thermal stripping), or using part of the ammonia available in the solution, as a stripping agent (ammonia stripping). Accordingly, the term of self-stripping urea plant is used in this description to denote a urea plant comprising a high-pressure thermal stripping section or ammonia stripping section.

The MP section and the LP section serve substantially to decompose unreacted carbamate and recycle ammonia from the urea aqueous solution leaving the HP section. The urea aqueous solution leaving the LP section, and having a concentration usually around 70-80%, may be directed to a finishing section such as a granulation apparatus or a prilling tower, for a further concentration and conversion into a solid product.

Some self-stripping urea plants include a plurality of urea production lines in parallel, each urea production line including a respective high-pressure section, medium-pressure section, low-pressure section and possibly a respective finishing section. Said urea production lines in parallel are usually identical or substantially identical to each other.

The carbon dioxide is fed to the high-pressure section (or sections, if more than one) via a suitable compression section. Due to the need of compressing a gaseous medium to a high pressure well over 100 bar, said CO2 compression section typically includes several compression stages and is a significant source of cost and energy consumption.

The self-stripping urea plants account for a large portion of the current production of urea and are installed worldwide. There is a strong interest in the revamping of existing self-stripping urea plants, especially to increase their capacity, that is the production of urea (MTD, metric tons of urea per day).

The simplest way to increase the urea production is to increase the input of ammonia and carbon dioxide (more in more out); in most cases, however, the existing equipments, especially those of the HP section and MP section, provide a very limited margin for additional flow rate and, as a consequence, this approach is not applicable. Other solutions have been proposed in this respect, for example EP-A-2397463 discloses the addition of a medium-high pressure section between the existing HP section and MP section, where urea solution leaving the high pressure section is at least partly redirected to said newly-installed section.

The revamping of an existing self-stripping urea plant poses a number of problems including: the need of expensive revamping of the high-pressure and/or medium-pressure section; the need of additional equipment (e.g. new pumps) to deal with increased flow rates; the limited room available on the site.

SUMMARY OF THE INVENTION

The purpose of the invention is to provide a novel method for increasing the performance of an existing self-stripping urea plant.

The idea underlying the invention is to install a new synthesis section which operates according to the CO2-stripping process. This new section produces a urea solution which is treated preferably in the available LP section of the existing plant.

Hence the above purpose is reached with a method for revamping a self-stripping urea plant, said plant comprising: a high pressure urea synthesis section including at least a reactor, a thermal stripper or an ammonia stripper and a condenser; a medium pressure treatment section; a low pressure recovery section, the method being characterized by the following steps:

installation of a CO2-stripping synthesis section, where ammonia and carbon dioxide are converted to an aqueous urea solution according to CO2-stripping process, at least a portion the aqueous urea solution leaving said new CO2-stripping section is directed to said existing low pressure recovery section, by-passing the existing self-stripping high-pressure section and medium pressure treatment section.

The CO2-stripping process and the related equipments are known to a skilled person. A description can be found e.g. in the Ullmann's Encyclopedia of industrial chemistry, Wiley-VCH Verlag, p. 669-674. Accordingly, a CO2-stripping synthesis section is understood as including at least a urea reactor, a stripper for unconverted reactants where carbon dioxide is used as a stripping medium, a carbamate condenser and optionally a reactor off-gas scrubber. Said reactor, stripper, carbamate condenser and (if provided) said optional scrubber form a loop and operate substantially at the same pressure, which is usually in the range 120-150 bar. The stripper is preferably implemented as a vertical falling-film tube heat exchanger, where the urea solution coming from the reactor flows inside vertical tubes, heat is supplied to the outside of the tubes for example with medium-pressure steam, and fresh carbon dioxide flows counter-currently to the urea solution inside the tubes, thus acting as a stripping medium and promoting the transfer of ammonia from the liquid phase to the gaseous phase.

The new CO2-stripping synthesis section operates substantially in parallel to the existing self-stripping synthesis section.

The self-stripping plants normally provide the recycle of a flow of liquid ammonia and of a flow of a carbamate solution from the medium-pressure section to the high-pressure section. According to a preferred embodiment of the invention, a portion of said liquid ammonia and/or a portion of said carbamate solution are redirected to the new CO2-stripping section, in order to provide the necessary ammonia input.

When the existing self-stripping urea plant comprises two or more urea production lines in parallel, each line having its own high, medium and low-pressure section, a preferred embodiment of the invention provides that the aqueous urea solution produced in the new CO2-stripping section is divided between some or all of the available low-pressure sections. Accordingly, the solution leaving said CO2-stripping section, and by-passing the MP sections, is split into a plurality of streams, and each of said streams is directed to a respective low-pressure recovery section.

Similarly, respective portions of liquid ammonia and/or carbamate solution, recovered from the medium-pressure sections of a multiple-line plant, can be directed to the new CO2 stripping section.

When the direction or the redirection of a stream is mentioned, it shall be understood that the invention includes the provision and the installation of the related flow-control means such as pipes, valves, etc. These details are not described since they pertain to customary practice for a skilled person.

A great advantage of the invention is that the capacity can be increased without an increased duty of the existing HP and MP sections, which are by-passed by the additional urea solution. This additional solution is sent directly to the LP section, which is usually able to tolerate an increased flow rate, more than the HP and MP sections which are commonly operated at (or very close to) their maximum capacity. Once the revamping is complete, the HP and MP sections of the self-stripping line(s) may operate substantially at the same conditions as before, the additional capacity being provided by the newly-installed CO2-stripping high-pressure section.

When applicable, some of the urea solution from the CO2 stripping section may be directed to the existing medium-pressure section. This is typically the case when the MP section provides a residual margin for processing an additional flow rate. In most cases, this part of urea solution directed to the MP section will be, however, a minor part. Accordingly, a greater part of said urea solution (more than 50%) bypasses the MP section and flows to the LP section.

Further to the above, the applicant has found another important and unexpected advantage in that the conversion yield of the existing self-stripping HP section is improved, because less water is found in the reactor. The reason can be summarized as follows.

The urea solution leaving the new CO2-stripping section contains a low amount of unconverted free ammonia, due to intensive stripping with the fresh carbon dioxide. By feeding this low-ammonia urea solution to the LP section, the invention provides a compensation for the ammonia excess which, on the other hand, is a drawback of the self-stripping plants. In most cases, the existing LP section (before revamping) receives a urea solution with a considerable excess of ammonia compared to the stoichiometric amount for the formation of urea, that is to say, the nitrogen to carbon ratio (N/C) is higher than optimum. For this reason, the LP section needs a considerable amount of water to condensate and recycle said excess of ammonia. After a revamping according to the invention, the low-ammonia urea solution coming from the new section will adjust the N/C ratio to a lower value, thus reducing the water feed to the LP section. This is an advantage in terms of cost for the water feeding but, most important, will lead to less specific production of carbamate (relative to the capacity in terms of urea produced) and, since the carbamate is recycled as aqueous solution, less water introduced in the HP synthesis section. Water is detrimental to the yield of conversion, as water is a by-product of the conversion, which means that all the above results in a better conversion.

To summarize, the inventive addition of a CO2-stripping section can provide not only an increased capacity, without additional duty for the existing HP/MP sections, but also a positive effect on the yield of the existing HP synthesis section thanks to an advantageous re-balancing of the N/C ratio in the LP section.

DETAILED DESCRIPTION OF PREFERRED EMBODIMENTS

Figure 1:
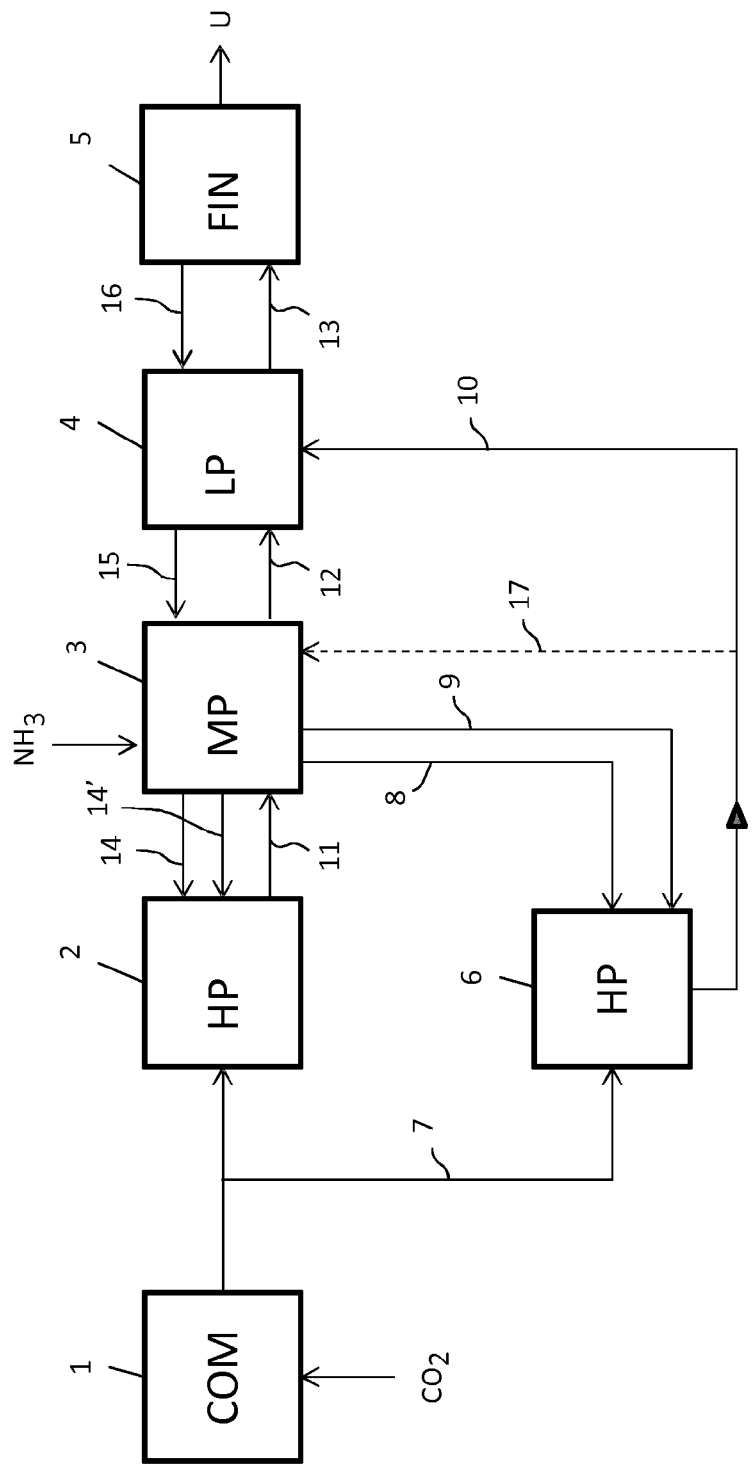
FIG. 1 is a scheme of a self-stripping urea plant revamped in accordance with an embodiment of the invention.

Referring to FIG. 1, the block 1 denotes a carbon-dioxide compression section and blocks 2 to 5 denote a conventional self-stripping urea plant. More in detail, block 2 denotes a self-stripping HP section, block 3 is a medium-pressure section, block 4 is a low-pressure recovery section and block 5 is an optional finishing section.

These sections are known in the art and need not be described in a full detail. Basically, the high-pressure section 2 comprises a reactor, a thermal stripper or ammonia stripper, and a condenser; the medium pressure section 3 normally comprises a decomposition section and an ammonia recovery section; the low pressure section 4 comprises another decomposition section and an ammonia recovery section, operating at a lower pressure.

The finishing section 5 may include a vacuum concentration section and equipments suitable for the conversion of concentrated urea into a solid product U, such as a granulator or a prilling tower.

Usually the section 2 is run at a pressure of around 120-140 bar, the section 3 at around 20 bar and the section 3 at around 2-4 bar, but these values may vary according to the particular plant which is revamped.

FIG. 1 shows also the inputs of fresh carbon dioxide CO2 and the input of fresh ammonia NH3. The fresh ammonia may enter the medium-pressure section 3 (as shown) and thereafter reach the reactor of section 2 together with ammonia recovered from the MP section 3 and LP section 4.

The invention provides the installation of a CO2-stripping synthesis section 6, where ammonia and carbon dioxide are converted to an aqueous urea solution according to the known CO2-stripping process.

Said new section 6 receives a carbon dioxide input 7 from the existing carbon-dioxide compression section 1, although in some embodiments, if necessary, a new compression section may be installed or the existing one may be revamped.

Ammonia input for said section 6 is given by an ammonia flow 8 and a flow of carbamate 9 coming from the existing MP section 3, which means that at least part of the ammonia and carbamate obtained in said section 3 (originally directed to the section 2) will be redirected to the new CO2-stripping section 6.

In some cases, fresh ammonia may also be fed to the new CO2-stripping section 6. Anyway, the way of feeding fresh ammonia is not essential for the invention.

Said new section 6 operates at a high pressure which is preferably the same pressure (or substantially the same pressure) of the section 2. As mentioned before, said pressure is preferably in the range 120 to 150 bar and more preferably is around 140 bar.

The aqueous urea solution 10 leaving said CO2-stripping section 6, as shown, is directed to the low pressure recovery section 4, by-passing the existing self-stripping high-pressure section 2 and the medium pressure treatment section 3. In some embodiments of the invention, a portion of the urea solution leaving the CO2-stripping section 6 may be also directed to the medium-pressure section 3, as shown by the dotted flow line 17. This embodiment may be applied, for example, when the available MP section is still able to cope with a certain increase of capacity. Since, however, the margin of the MP section, if any, will be limited, the portion of said urea solution directed to the LP section 4 is normally greater than the portion sent to the MP section 3.

It should be noted that the urea solution 10 has a low content of ammonia, compared to the effluent of the original HP section 2 which, in most cases, contains a large ammonia excess. Hence, an advantageous effect of the invention is that the N/C ratio in the LP section 4 is lowered and, as explained above, less water will be found in the reactor of section 2, to the advantage of the conversion yield.

Figure 2:
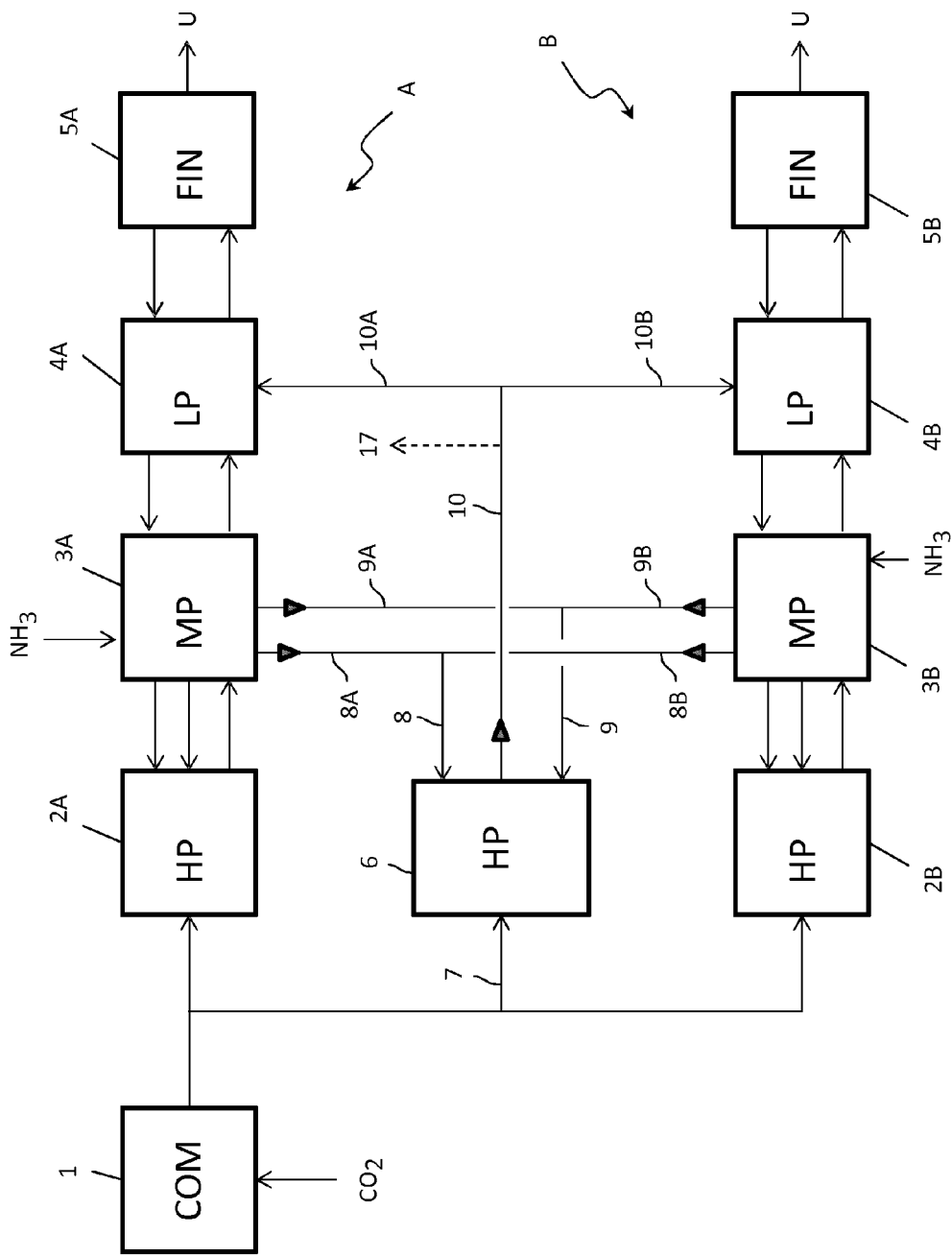
FIG. 2 is a scheme of a self-stripping urea plant with two lines in parallel, which is also revamped according to another embodiment.

FIG. 2 shows an example of a preferred application of the invention to a urea plant with several production lines in parallel. Two lines A, B are shown, but the invention is equally applicable with any number of urea production lines in parallel.

Each line includes a high-pressure section 2A, 2B, a medium-pressure section 3A, 3B, a low pressure section 4A, 4B and optionally a finishing section 5A, 5B. The compression section 1 may be separate or in common. In each line A, B, the flows exchanged between said sections are similar to FIG. 1 and, hence, they are not described in detail.

The urea effluent 10 from the new section 6, and bypassing the MP sections, is split into a first part 10A directed to the low pressure section 4A of the first line, and a second part 10B directed to the low pressure section 4B of the second line. Similarly, the ammonia input to the section 6 is provided by respective streams 8A, 8B of ammonia and 9A, 9B of carbamate, coming from the medium-pressure sections of the urea lines A and B. In some cases, as mentioned above, fresh ammonia may also be fed to the new CO2-stripping section 6.

In a similar way, the invention can be applied to plants with any number of urea production lines. Also in the embodiment of FIG. 2, some of the urea effluent from the new section 6 may be directed to one or more of the medium-pressure section(s), whenever it is possible and deemed appropriate, as denoted by line 17.

Turning back to FIG. 1, the lines 11 and 12 denote the aqueous solution of urea from the HP section 2 to the MP section 3 and from the latter to the LP section 4. The flow line 13 indicates the concentrated urea (usually around 70%) leaving the LP section 4, which can be exported as such or further processed in the finishing section 5.

The lines 14 and 14' denotes generally the recycle from the MP section to the HP synthesis section, which may comprise: a first current of liquid ammonia stream which is mixed with a fresh ammonia input and fed to the high-pressure reactor of the section 2; a second current comprising the bottom solution of a rectifying column, which is mixed with overhead vapors of the high-pressure stripper and sent to the high-pressure condenser of the section 2. Said two currents, denoted by the lines 14 and 14', may be mixed in some embodiments.

The line 15 denotes a recycle from LP to MP section, which may consist predominantly of ammonia-rich carbonate solution condensed in a low pressure condenser of said LP section 4. The line 16 denotes a further current of carbonate solution which is recycled from the finishing section 5, for example in a vacuum concentration section.

The invention claimed is:

1. A method for revamping a self-stripping urea plant, said plant comprising: a high pressure urea synthesis section including at least a reactor, a thermal stripper or an ammonia stripper and a condenser; a medium pressure treatment section; a low pressure recovery section, the method comprising the following steps:
   installation of a $CO_2$-stripping synthesis section, where ammonia and carbon dioxide are converted to an aqueous urea solution according to $CO_2$-stripping process,
   wherein said new $CO_2$-stripping section comprises at least: a synthesis reactor, a stripper, and a condenser, which are part of a high-pressure loop, and
   wherein at least a portion of the aqueous urea solution leaving said new $CO_2$-stripping section is directed to said existing low pressure recovery section, by-passing the existing self-stripping high-pressure section and medium pressure treatment section.

2. The method according to claim 1, wherein said new $CO_2$-stripping section further comprises a scrubber.

3. The method according to claim 1, said high-pressure loop operating substantially at the same pressure as the existing self-stripping synthesis section.

4. The method according to claim 1, wherein a first portion of the aqueous urea solution leaving said new $CO_2$-stripping section is directed to said low pressure recovery section, while a second remaining portion of said solution is directed to said medium pressure treatment section.

5. The method according to claim 4, said first portion of urea solution being greater than said second portion.

6. The method according to claim 1, wherein a portion of liquid ammonia and/or a portion of carbamate solution, which are recovered from the existing medium-pressure section, is fed to the new $CO_2$-stripping section.

7. The method according to claim 6, wherein said portion of liquid ammonia and/or portion of carbamate is fed to said $CO_2$-stripping section via existing pumps of the self-stripping plants.

8. The method according to claim 1, wherein: the existing self-stripping urea plant comprises more than one urea production lines in parallel, the aqueous urea solution leaving said new $CO_2$-stripping section and by-passing the medium-pressure sections is split into a plurality of streams, and each of said streams is directed to a respective low-pressure recovery section of the existing urea production lines.

9. The method according to claim 8, wherein some of the urea solution from the new $CO_2$ stripping section is also directed to one or more of the medium-pressure sections.

10. The method according to claim 8, wherein respective portions of liquid ammonia and/or carbamate solution, recovered from the medium-pressure sections of the urea production lines, are directed to the new $CO_2$ stripping section.

* * * * *